United States Patent
Hara et al.

(10) Patent No.: US 10,912,954 B2
(45) Date of Patent: Feb. 9, 2021

(54) PATIENT SHUTTLE SYSTEM, IRRADIATION SYSTEM FOR PARTICLE THERAPY AND OPERATION METHOD THEREOF

(71) Applicant: B dot Medical Inc., Tokyo (JP)

(72) Inventors: Yousuke Hara, Chiba (JP); Takuji Furukawa, Chiba (JP); Eri Takeshita, Chiba (JP); Kota Mizushima, Chiba (JP)

(73) Assignee: B DOT MEDICAL INC., Tokyo (JP)

( * ) Notice: Subject to any disclaimer, the term of this patent is extended or adjusted under 35 U.S.C. 154(b) by 0 days.

(21) Appl. No.: 16/692,068

(22) Filed: Nov. 22, 2019

(65) Prior Publication Data

US 2020/0306563 A1    Oct. 1, 2020

(30) Foreign Application Priority Data

Mar. 29, 2019    (JP) .................................. 2019-065824

(51) Int. Cl.
*A61N 5/10*        (2006.01)

(52) U.S. Cl.
CPC ......... *A61N 5/1081* (2013.01); *A61N 5/1045* (2013.01); *A61N 5/1049* (2013.01);
(Continued)

(58) Field of Classification Search
CPC .. A61N 5/1077; A61N 5/1049; A61N 5/1069; A61N 2005/1061;
(Continued)

(56) References Cited

U.S. PATENT DOCUMENTS

| 5,483,960 | A  | * | 1/1996 | Steiger | A61B 6/482 |
| | | | | | 378/54 |
| 6,292,534 | B1 | * | 9/2001 | Linders | A61B 6/4233 |
| | | | | | 348/E5.086 |

(Continued)

FOREIGN PATENT DOCUMENTS

| EP | 1749550 A1 | 2/2007 |
| EP | 3061498 A1 | 8/2016 |

(Continued)

OTHER PUBLICATIONS

Japanese Office Action, issued in Application No. 2019-065824, dated Jun. 25, 2019.
(Continued)

*Primary Examiner* — David A Vanore
(74) *Attorney, Agent, or Firm* — Birch, Stewart, Kolasch & Birch, LLP (57) ABSTRACT

A patient shuttle system, an irradiation system for particle therapy and an operation method thereof are provided. One embodiment of the present invention provides a patient shuttle system including a patient table on which a patient is placed, a drive device that causes the patient table to move parallel and/or rotate, and a drive control device that controls parallel movement and/or rotation of the patient table by the drive device, in accordance with a parallel movement amount and/or a rotation amount of the patient table that are received from a patient positioning system provided in a treatment room for particle therapy.

9 Claims, 9 Drawing Sheets

(52) U.S. Cl.
CPC ......... *A61N 5/1065* (2013.01); *A61N 5/1069* (2013.01); *A61N 2005/1052* (2013.01); *A61N 2005/1061* (2013.01); *A61N 2005/1087* (2013.01)

(58) Field of Classification Search
CPC .......... A61N 2005/1097; A61N 5/1082; A61N 2005/1074; A61N 5/103; A61N 5/1064; A61N 5/1083; G21K 5/04; G21K 1/093; G21K 1/08; G21K 1/025; A61B 6/587; A61B 2034/2055; A61B 34/20; A61B 6/0407; A61B 6/08; A61B 6/12
USPC ..... 250/393, 208.1, 370.09, 396 ML, 396 R; 378/98.8, 116, 15, 205, 210, 54, 62, 901, 378/91, 98.2
See application file for complete search history.

(56) References Cited

U.S. PATENT DOCUMENTS

| | | | | |
|---|---|---|---|---|
| 7,734,009 | B2* | 6/2010 | Brunner | G06T 11/005 378/62 |
| 8,848,872 | B2* | 9/2014 | Lee | G03B 42/04 378/91 |
| 8,908,950 | B2* | 12/2014 | Barfuss | G06T 11/006 382/131 |
| 9,108,048 | B2* | 8/2015 | Maurer, Jr. | A61B 8/4416 |
| 9,610,056 | B2* | 4/2017 | Lavallee | A61B 6/584 |
| 9,788,810 | B2* | 10/2017 | Ancar | A61B 6/542 |
| 9,968,321 | B2* | 5/2018 | Wikler | A61B 6/488 |
| 10,029,124 | B2* | 7/2018 | Lee | A61B 6/032 |
| 10,143,417 | B2* | 12/2018 | Danielsson | A61B 6/5217 |
| 10,201,717 | B2* | 2/2019 | Berlinger | A61N 5/1049 |
| 10,213,624 | B2* | 2/2019 | Lee | A61B 6/032 |
| 10,431,418 | B1* | 10/2019 | Mizushima | A61N 5/1077 |
| 10,589,128 | B2* | 3/2020 | Michaud | A61N 5/1037 |
| 10,667,869 | B2* | 6/2020 | Kotian | A61B 90/13 |
| 10,684,380 | B2* | 6/2020 | Lee | A61B 6/4266 |
| 2008/0006776 | A1* | 1/2008 | Furukawa | G21K 5/04 250/396 R |
| 2010/0213384 | A1* | 8/2010 | Furukawa | A61N 5/1043 250/396 ML |
| 2012/0305790 | A1* | 12/2012 | Hanawa | A61N 5/1043 250/393 |
| 2015/0133714 | A1* | 5/2015 | Inaniwa | G21K 5/04 600/1 |
| 2015/0328482 | A1* | 11/2015 | Hishikawa | A61N 5/1045 250/393 |
| 2017/0229281 | A1* | 8/2017 | Furukawa | G21K 1/093 |

FOREIGN PATENT DOCUMENTS

| | | |
|---|---|---|
| JP | 2000-288102 A | 10/2000 |
| JP | 2007-289373 A | 11/2007 |
| JP | 2008-237687 A | 10/2008 |
| JP | 2012-148026 A | 8/2012 |
| JP | 2014-61445 A | 4/2014 |
| JP | 2014-161623 A | 9/2014 |
| JP | 2017-140526 A | 8/2017 |

OTHER PUBLICATIONS

Extended European Search Report for European Application No. 19211627.5, dated Apr. 30, 2020.

* cited by examiner

↓ MOVE PATIENT TABLE 11, AND OBTAIN X-RAY IMAGE

*Fig. 8B*

↓ MOVE PATIENT TABLE 11, AND OBTAIN X-RAY IMAGE

*Fig. 8C*

↓ COMPLETE POSITIONING

PATIENT SHUTTLE SYSTEM, IRRADIATION SYSTEM FOR PARTICLE THERAPY AND OPERATION METHOD THEREOF

BACKGROUND OF THE INVENTION

Field of the Invention

The present invention relates to a patient shuttle system, an irradiation system for particle therapy and an operation method thereof.

Description of the Related Art

In particle therapy, a treatment method is carried out that irradiates a lesion or a tumor portion such as a cancer or the like (target) with particle beams such as proton beams, heavy-ion beams or neutron beams that are taken out from an accelerator. In order to suppress an influence on normal tissue while increasing concentration of a particle beam dose to the target, the target is irradiated with the particle beams with high precision.

Figure 9A:
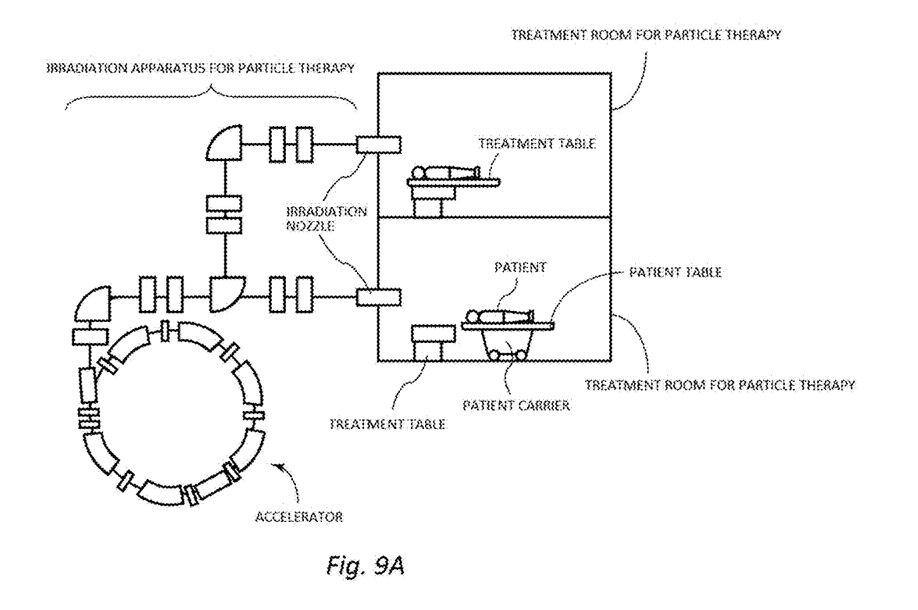
FIGS. 9A, 9B and 9C are views explaining a conventional irradiation system for particle therapy.

Conventionally, before irradiating a patient with a particle beam, the patient is placed on a treatment table placed in a room (hereinafter, referred to as a "treatment room for particle therapy") where an irradiation nozzle of the particle beam is installed and particle therapy is performed, and alignment of a position of the particle beam irradiated from the irradiation nozzle and a site which should be irradiated with the particle beam (referred to as "patient positioning") is performed. In other words, the particle-beam-irradiated position and the patient position are adjusted so that the particle beam irradiated from the irradiation nozzle is applied to the target in the patient with high precision (FIG. 9A).

In the patient positioning, first of all, in order to suppress a deviation between the patient and the treatment table, the patient is fixed onto the patient table of the treatment table with use of an immobilization device. Next, rough alignment of the position where particle beam is irradiated and the site which should be irradiated with the particle beam is performed from above the skin of the patient by using a laser pointer or the like that is installed in the treatment room for particle therapy. Thereafter, the patient is exposed with an X-ray, an X-ray image is obtained, the position, inclination and the like of the patient table where the patient is placed are adjusted while watching the X-ray image, and the position where the particle beam is irradiated is determined with high precision (in units of millimeters, for example). Subsequently, after the patient positioning, the therapy with the particle beam is started.

In general, patient positioning takes several minutes to several tens of minutes, and occupies most of the treatment time of particle therapy. Patient positioning for a long time in the particle beam treatment room also increases the occupancy time of the treatment room for particle therapy per patient. As a result, the number of treated patients per unit time cannot be increased, the time to perform Quality Assurance (QA) measurement of particle beams to ensure safe treatment irradiation is squeezed, and the burden on medical workers such as doctors, nurses, and radiographers is increased.

Japanese Patent Laid-Open No. 2000-288102 discloses a method of performing patient positioning in a preparation room which is separated from the treatment room for particle therapy where an irradiation nozzle is installed for the purpose of reducing the time required for patient positioning. In the method, the first patient is placed on the first bed and an immobilization device is attached to the patient in the preparation room, rough alignment of the patient position is performed by using a laser pointer, after which, the first bed with the patient placed thereon is transported to a simulation room along a first transport path, and precise alignment of the patient is performed. At this time, in the preparation room from which the patient is carried out, the next patient is placed on the second bed, and similar patient positioning is performed. The first patient for whom precise alignment is performed in the simulator room is transported to the treatment room for particle therapy along the second transport path while being placed on the first bed, and irradiation for therapy is performed. In this way, a working burden in the treatment room for particle therapy is reduced, and particle therapy is efficiently advanced.

Figure 9B:
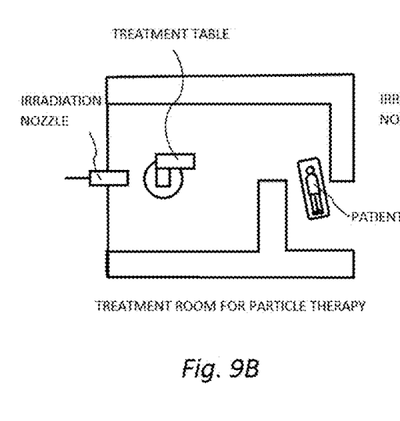
Figure 9C:
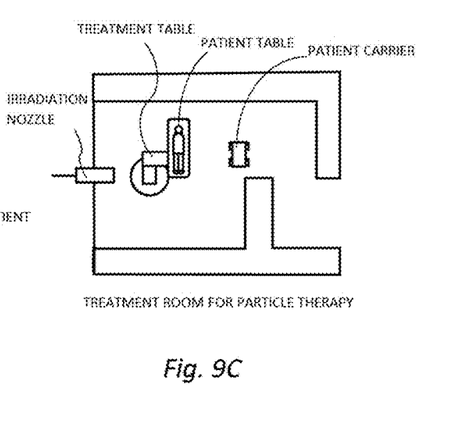

Japanese Patent Laid-Open No. 2012-148026 discloses a method of transferring only a patient table portion where a patient is placed onto the treatment table in the treatment room for particle therapy where the irradiation nozzle is installed. In the method, positioning of the patient who is placed on the patient table in the preparation room is performed, the patient table where the patient is placed is placed on a transportation table, and the patient table is transported to the treatment room from the preparation room. In the treatment room for particle therapy, only the patient table portion where the patient is placed is transferred onto the treatment table in the treatment room for particle therapy, and particle therapy is performed (FIGS. 9B and 9C).

In the art of Japanese Patent Laid-Open No. 2000-288102, it is difficult to transport a patient to the treatment room for particle therapy while keeping a state of the patient positioning which is performed in the preparation room, and the position of the patient deviates due to vibration or the like during transport, so that it is actually necessary to perform positioning again in the treatment room for particle therapy. In the art of Japanese Patent Laid-Open No. 2012-148026, after the patient positioning is performed in the preparation room, only the patient table portion where the patient is placed is transferred onto the treatment table installed in the treatment room for particle therapy, and there is a fear that the position deviates during the transfer. Further, in order to always have fixed treatment tables in the treatment room for particle therapy, it is necessary to make the treatment room for particle therapy as large as the number of treatment tables, and there is a problem that installation of the equipment for QA measurement is hindered by the treatment tables at the time of QA measurement or the like.

In the light of the situation as above, the present invention has an object to provide a patient shuttle system, an irradiation system for particle therapy and an operation method thereof.

SUMMARY OF THE INVENTION

The present invention includes the following aspects.

[1] A patient shuttle system, comprising:

a patient table on which a patient is placed;

a drive device configured to cause the patient table to move parallel and/or rotate;

a drive control device configured to control parallel movement and/or rotation of the patient table by the drive device, in accordance with a parallel movement amount and/or a rotation amount of the patient table that are received from a patient positioning system provided in a treatment room for particle therapy; and a base lock mechanism configured to engage with a lock receiving member provided in the treatment room for particle therapy and fix the patient shuttle system to the treatment room for particle therapy.

[2] The patient shuttle system according to the above [1], wherein the drive device is configured to cause the patient table to move parallel along at least one direction of a short side direction (an X-axis) of the patient table, a long side direction (a Y-axis) of the patient table, and a perpendicular direction (a Z-axis) to the long side direction and the short side direction, and/or cause the patient table to rotate around at least one direction of the short side direction (the X-axis), the long side direction (the Y-axis), and the perpendicular direction (the Z-axis).

[3] The patient shuttle system according to the above [1], wherein the drive device is configured to cause the patient table to move parallel along a short side direction (an X-axis) of the patient table, a long side direction (a Y-axis) of the patient table, and a perpendicular direction (a Z-axis) to the long side direction and the short side direction, and cause the patient table to rotate around the short side direction (the X-axis), the long side direction (the Y-axis), and the perpendicular direction (the Z-axis).

[4] The patient shuttle system according to the above [1], wherein a particle beam is a proton beam, a neutron beam, or a heavy-ion beam.

[5] The patient shuttle system according to the above [1], wherein the patient shuttle system is applicable to transporting a patient to the treatment room for particle therapy and/or to transporting a patient from the treatment room for particle therapy.

[6] An irradiation system for particle therapy, comprising
an irradiation apparatus for particle therapy;
a patient positioning system provided in a treatment room for particle therapy;
and the patient shuttle system according to the above [1].

[7] The irradiation system for particle therapy according to the above [6],
wherein the patient positioning system comprises
an X-ray image pickup control device configured to control an X-ray generating apparatus and an X-ray detector and generate an X-ray image of the patient, the X-ray generating apparatus being configured to irradiate a patient placed on the patient table with an X-ray, and the X-ray detector being configured to detect the X-ray,
a patient positioning device configured to compare the X-ray image with a reference X-ray image relating to a site that should be irradiated with a particle beam, of the patient, and calculate a positional error between the X-ray image and the reference X-ray image, and
a shuttle system control device configured to calculate a parallel movement amount and/or a rotation amount of the patient table so as to reduce the positional error, when the positional error is not a predetermined allowable value or less, and transmit the parallel movement amount and/or the rotation amount to the patient shuttle system.

[8] An operation method of the irradiation system for particle therapy according to the above [7], comprising the steps of:
the X-ray image pickup control device controlling the X-ray generating apparatus and the X-ray detector, and generating an X-ray image of the patient;
the patient positioning device comparing the X-ray image with the reference X-ray image and calculating a positional error between the X-ray image and the reference X-ray image;

the shuttle system control device calculating a parallel movement amount and/or a rotation amount of the patient table so as to reduce the positional error, when the positional error is not a predetermined allowable value or less, and transmitting the parallel movement amount and/or the rotation amount to the patient shuttle system; and
the drive control device controlling parallel movement and/or rotation of the patient table by the drive device, in accordance with the parallel movement amount and/or the rotation amount.

[9] The method according to the above [8], further comprising the steps of:
the shuttle system control device receiving an error signal from the patient shuttle system;
the patient positioning device transmitting the error signal to a therapy control apparatus configured to supervise the irradiation system for particle therapy; and
the therapy control apparatus stopping irradiation of the particle beam through a particle beam irradiation control apparatus configured to control the irradiation apparatus for particle therapy.

[10] A patient shuttle system for transporting a patient to a treatment room for particle therapy and/or for transporting a patient from the treatment room for particle therapy, comprising:
a drive device configured to cause a patient table to move parallel and/or rotate;
a drive control device configured to control parallel movement and/or rotation of the patient table by the drive device, in accordance with a parallel movement amount and/or a rotation amount of the patient table that are received from a patient positioning system provided in the treatment room for particle therapy; and
a base lock mechanism configured to engage with a lock receiving member provided in the treatment room for particle therapy and fix the patient shuttle system to the treatment room for particle therapy.

[11] The patient shuttle system for transporting a patient to the treatment room for particle therapy and/or for transporting a patient from the treatment room for particle therapy, according to the above [1],
wherein the patient positioning system comprises:
an X-ray image pickup control device configured to control an X-ray generating apparatus and an X-ray detector and generate an X-ray image of the patient, the X-ray generating apparatus, being configured to irradiate a patient placed on the patient table with an X-ray, and the X-ray detector being configured to detect the X-ray,
a patient positioning device configured to compare the X-ray image with a reference X-ray image relating to a site that should be irradiated with a particle beam, of the patient, and calculate a positional error between the X-ray image and the reference X-ray image, and
a shuttle system control device configured to calculate a parallel movement amount and/or a rotation amount of the patient table so as to reduce the positional error, when the positional error is not a predetermined allowable value or less, and transmit the parallel movement amount and/or the rotation amount to the patient shuttle system.

DETAILED DESCRIPTION OF THE PREFERRED EMBODIMENT

[Patient shuttle system]

A patient shuttle system 10 according to one embodiment of the present invention will be described.

Figure 1A:
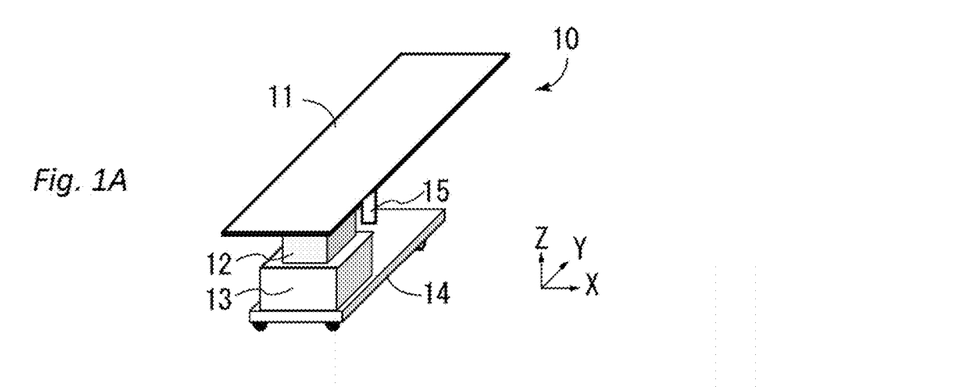
FIGS. 1A, 1B and 1C are schematic views of a patient shuttle system according to one embodiment of the present invention.
Figure 1B:
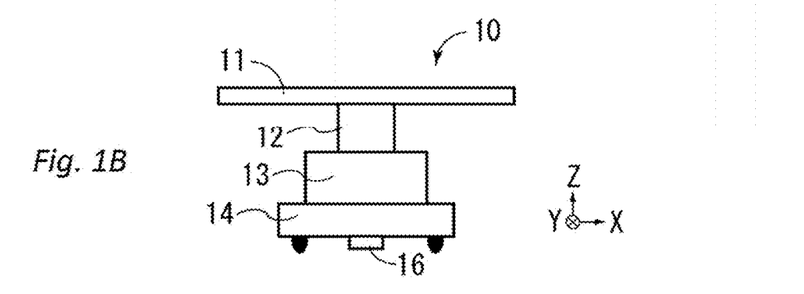
Figure 1C:
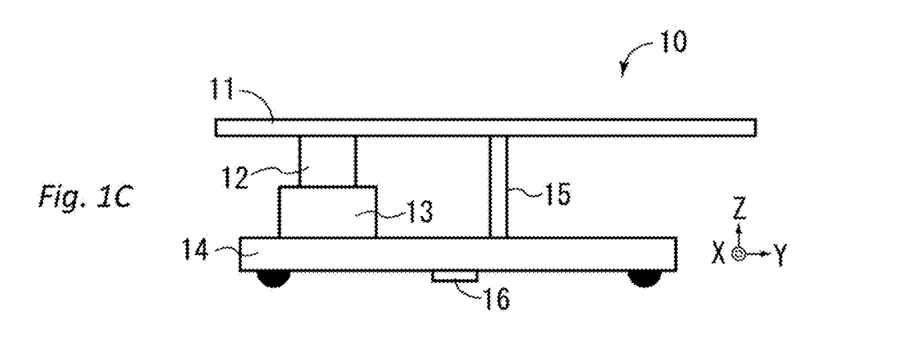

FIG. 1A is a schematic perspective view of the patient shuttle system 10, FIG. 1B is a schematic front view, and FIG. 1C is a schematic side view. As illustrated in FIGS. 1A to 1C, a short side direction of a patient table 11 in a rectangular shape is set as an X-axis, a long side direction of the patient table 11 is set as a Y-axis, and a height direction (a direction perpendicular to the X-axis and the Y-axis) of the patient shuttle system 10 is set as a Z-axis. Note that a shape of the patient table 11 is not limited to a rectangular shape, but may be an oval shape (in this case, a short axis is the X-axis that is the short side direction, a long axis is the Y-axis that is the long side direction, and an axis perpendicular to both the axes is the Z-axis), and can be a shape in which the patient can be stably placed.

The patient shuttle system 10 includes the patient table 11 where a patient is placed, a drive device 12 that is configured to cause the patient table 11 to move parallel along the respective axes and/or rotate around the respective axes, a drive control device 13 that is configured to control the drive device 12, and a base 14 that has the patient table 11, the drive device 12, and the drive control device 13 placed thereon, and has a plurality of casters for moving. A medical worker places the patient on the patient table 11, pushes the patient shuttle system 10 and can stably transport the patient to a treatment room for particle therapy. Note that the patient shuttle system 10 may be a self-propelled electric car.

The patient shuttle system 10 further includes a patient table lock mechanism 15 configured to hold (lock) a position (position before/after parallel movement, a position before/after rotation) of the patient table 11 stably, and a base lock mechanism 16 that is configured to fix the patient shuttle system 10 to the treatment room for particle therapy so that the patient shuttle system 10 does not move.

The patient table 11 includes immobilization devices (not illustrated) for fixing a body of a patient. The immobilization devices include a tool that fixes a head of a patient, tools that fix arms and legs of a patient, a tool that fixes a trunk of a patient, and/or a cushion member or the like that is formed along a shape of a body of a patient. Further, the patient table 11 may be configured so that a part of the patient table 11 such as portions corresponding to the head, legs and/or the trunk of a patient can incline. Further, breathing holes or the like may be provided in the patient table 11 so that a patient can be fixed even in a state of lying down on the patient table 11.

The drive device 12 includes motors for causing the patient table 11 to move parallel along the X-axis, the Y-axis and the Z-axis, motors for causing the patient table 11 to rotate around the X-axis, the Y-axis and the Z-axis, and mechanisms for transmitting drive forces of these motors to the patient table 11, in accordance with control by the drive control device 13. Further, the drive device 12 includes an encoder that detects rotation amounts, rotational speeds, rotation directions and the like of the respective motors, and output signals that are used to calculate a parallel moving amount and/or rotation amount of the patient table 11 to the drive control device 13.

Note that in the present embodiment, a mode in which the patient table 11 moves parallel along the X-axis, the Y-axis and the Z-axis, and rotates around the X-axis, the Y-axis, and the Z-axis by the drive device 12 will be described, but the present invention is not limited to this. A number of axes along and around which the patient table 11 performs parallel movement and rotation may be limited in accordance with a use purpose. In other words, the drive device 12 may be configured so that the patient table 11 can move parallel along at least one axis of the X-axis, the Y-axis, and the Z-axis, and/or can rotate around at least one axis of the X-axis, the Y-axis, and the Z-axis.

The drive device 12 is preferably configured to cause the patient table 11 to move parallel along the X-axis, the Y-axis, and the Z-axis, or cause the patient table 11 to rotate around the X-axis, the Y-axis, and the X-axis. The drive device 12 is more preferably configured to cause the patient table 11 to move parallel along the X-axis, the Y-axis, and the Z-axis, and to rotate around the X-axis, the Y-axis, and the Z-axis.

Figure 2A:
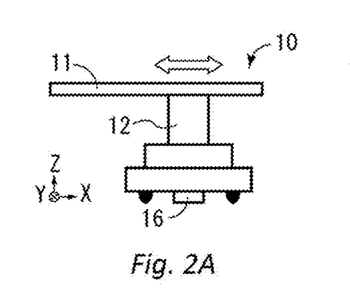
FIGS. 2A, 2B, 2C, 2D, 2E and 2F are views explaining parallel movement and rotation of the patient shuttle system.
Figure 2B:
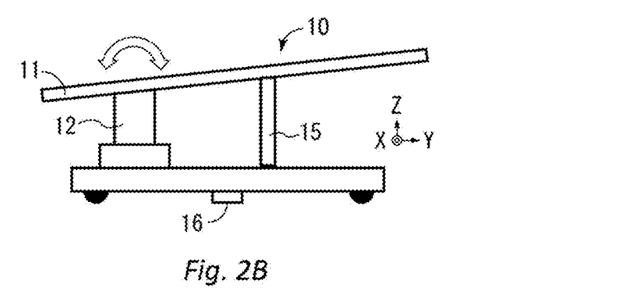
Figure 2C:
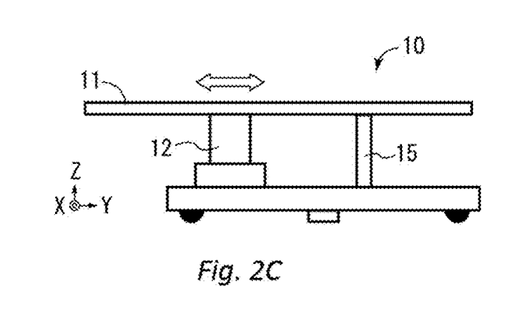
Figure 2D:
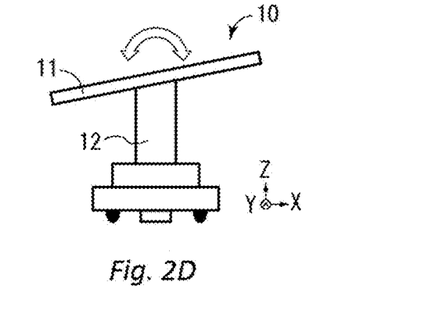
Figure 2E:
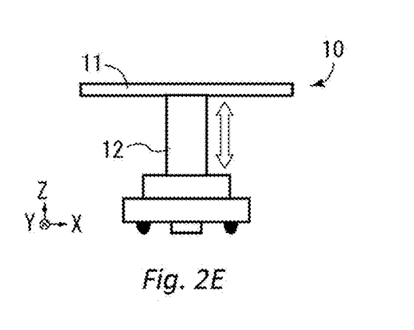
Figure 2F:
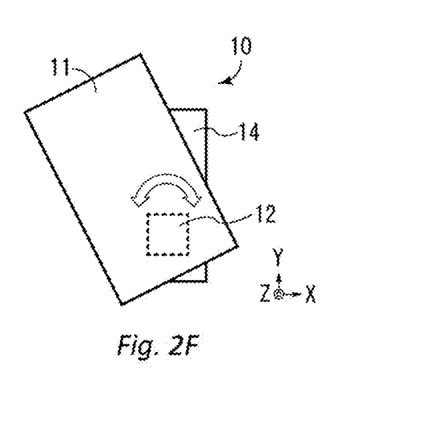

FIG. 2A shows parallel movement along the X-axis of the patient table 11, and FIG. 2B schematically shows rotation around the X-axis of the patient table 11. Likewise, FIG. 2C shows parallel movement along the Y-axis of the patient table 11, FIG. 2D shows rotation around the Y-axis of the patient table 11, FIG. 2E shows parallel movement along the Z-axis of the patient table 11, and FIG. 2F shows rotation around the Z-axis of the patient table 11.

The drive control device 13 is a computer including an interface such as an antenna that communicates wirelessly with a patient positioning system (described later) provided in the treatment room for particle therapy, or a port or the like that communicates with the patient positioning system by wire, a program and a processor (or ASIC or the like) for controlling the drive device 12 based on a signal from the patient positioning system, and a storage unit that stores the program and various kinds of information.

Figure 3:
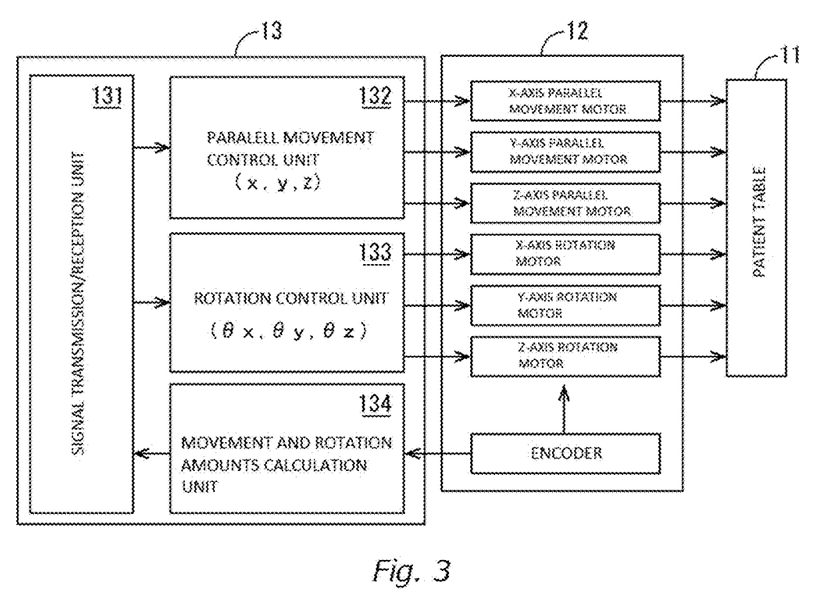
FIG. 3 is a control block diagram of the patient shuttle system.

FIG. 3 is a function block diagram of the drive control device 13. The drive control device 13 has a signal transmission/reception unit 131 that transmits and receives signals to and from the patient positioning system (reference sign 40 described later) that is provided in the treatment room for particle therapy, a parallel movement control unit 132 and a rotation control unit 133 that control the motors of the drive device 12, and a movement and rotation amounts calculation unit 134 that calculates parallel movement amounts (x, y, z) and/or rotation amounts ($\theta x$, $\theta y$, $\theta z$) of the patient table 11 based on outputs of the encoder of the drive device 12, as functional units that are realized by the program stored in the storage unit and the processor cooperating with each other.

The parallel movement control unit 132 controls an X-axis parallel movement motor that causes the patient table 11 to move parallel along the X-axis, a Y-axis parallel movement motor that causes the patient table 11 to move parallel along the Y-axis, and a Z-axis parallel movement motor that causes the patient table 11 to move parallel along the Z-axis, and controls the parallel movement amounts (x, y, z) of the patient table 11 along the respective axes.

The rotation control unit 133 controls an X-axis rotation motor that causes the patient table 11 to rotate around the X-axis, a Y-axis rotation motor that causes the patient table 11 around the Y-axis, and a Z-axis rotation motor that causes the patient table 11 to rotate around the Z-axis, and controls the rotation amounts (θx, θy, θz) of the patient table 11 around the respective axes.

The movement and rotation amounts calculation unit 134 receives information on the rotation amounts, rotation speeds, rotation directions and the like of the respective motors from the encoder of the drive device 12, and calculates the parallel movement amounts (x, y, z) and/or the rotation amounts (θx, θy, θz) of the patient table 11. Information on the parallel movement amounts (x, y, z) and/or the rotation amounts (θx, θy, θz) which are calculated is transmitted to the patient positioning system (reference sign 40 described later) through the signal transmission/reception unit 131.

The patient table lock mechanism 15 may be provided on the base 14 and configured to support the patient table 11 as illustrated in FIGS. 1A to 1C, or may be provided in the drive device 12, and configured to lock a mechanism that transmits the drive forces of the motors to the patient table 11. The patient table lock mechanism 15 is configured to hold the patient table 11 stably so that the patient table 11 does not move except for a time in which the patient table 11 is moving parallel and rotating. Accordingly, even when a power is not supplied to the drive device 12 for some reasons, the patient table lock mechanism 15 can stably hold the patient table 11, and therefore can prevent a situation such as the patient falling from the patient table 11. Note that the patient table lock mechanism 15 may be enabled to lock the patient table 11 at a timing instructed by a medical worker.

The base lock mechanism 16 is a mechanism configured to engage with a lock receiving member (reference sign 51 in FIGS. 5A and 5B) that is provided on a floor, a wall or the like in the treatment room for particle therapy, and fix the patient shuttle system 10 to the treatment room for particle therapy so that the patient shuttle system 10 does not move. The base lock mechanism 16 may be configured to be housed in the base 14 so that the base lock mechanism 16 does not get in the way at a time of the patient shuttle system 10 moving or the like, and to protrude from the base 14 at a time of engaging with the lock receiving member 51 in the treatment room for particle therapy. Note that when the lock receiving member 51 is provided on the wall of the treatment room for particle therapy, the base lock mechanism 16 may also be provided on a side of the base 14 accordingly.

[Irradiation system for particle therapy]

With use of FIG. 4A to FIG. 6, the irradiation system 20 for particle therapy for use in particle therapy using the patient shuttle system 10 will be described.

Figure 4A:
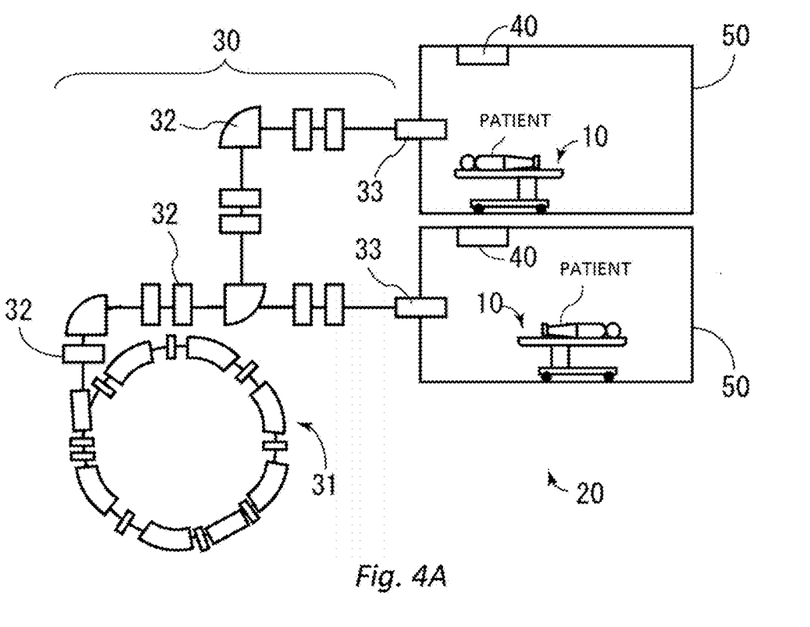
FIGS. 4A, 4B and 4C are schematic views of an irradiation system for particle therapy including the patient shuttle system.

The irradiation system 20 for particle therapy includes the patient shuttle system 10, the irradiation apparatus 30 for particle therapy, and the patient positioning system 40 provided in the treatment room 50 for particle therapy.

Note that a part of the patient positioning system 40 may be provided in the treatment room 50 for particle therapy, and a remaining part may be provided in a spot away from the treatment room 50 for particle therapy. Consequently, if a part of the patient positioning system 40, that is, at least an X-ray generating apparatus 41 and an X-ray detector 42 described later are provided in the treatment room 50 for particle therapy, the patient positioning system 40 is "the patient positioning system provided in the treatment room for particle therapy".

Further, in FIG. 4A, the irradiation system 20 for particle therapy that uses the one irradiation apparatus 30 for particle therapy in the two treatment rooms 50 for particle therapy is drawn, but the irradiation system 20 for particle therapy may be configured to use the one irradiation apparatus 30 for particle therapy in the one treatment room 50 for particle therapy, or may be configured to use the one irradiation apparatus 30 for particle therapy in the three or more treatment rooms 50 for particle therapy.

Figure 4B:
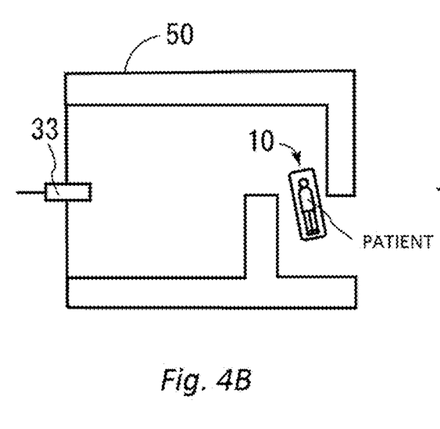
Figure 4C:
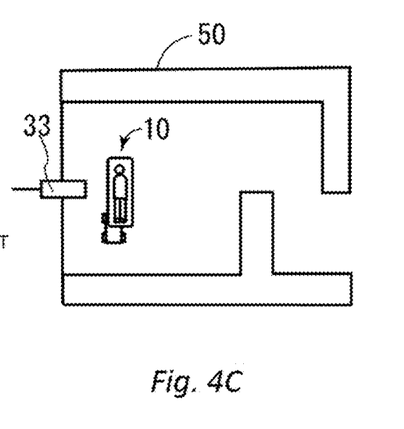

As illustrated in FIG. 4B and FIG. 4C, the patient shuttle system 10 where the patient is placed can be directly used as the treatment table for particle therapy after the patient shuttle system 10 is transported into the treatment room 50 for particle therapy from outside, and the base lock mechanism 16 is engaged with and fixed to the lock receiving member 51 provided on the floor of the treatment room 50 for particle therapy. Consequently, it is not necessary to transfer the patient to a treatment table in the treatment room for particle therapy from the shuttle system that transports the patient as in the prior art, and a burden on the patient is reduced. Further, because it is not necessary to always include a fixed treatment table in the treatment room 50 for particle therapy, a space of the treatment room 50 for particle therapy can be reduced, and a problem that the incorporated treatment table inhibits installation of a QA measurement device at the time of QA measurement or the like does not occur.

The irradiation apparatus 30 for particle therapy includes an accelerator 31 that generates a particle beam, a vacuum duct and various magnet units 32 that guide a particle beam, and an irradiation nozzle 33 that emits a particle beam to a site of a patient that should be irradiated.

The accelerator 31 is an apparatus that generates a particle beam, and is, for example, a synchrotron, a cyclotron, or a linear accelerator. The particle beam that is generated in the accelerator 31 passes through an inside of the vacuum duct, and is guided to the irradiation nozzle 33 by the various magnet units 32. The particle beam is a proton beam, a neutron beam or a heavy-ion beam.

The magnet units 32 may include a quadrupole magnet unit, a steering magnet unit, a bending magnet unit, and/or a focusing magnet or the like described in Japanese Patent No. 6364141 and Japanese Patent No. 6387476. The irradiation nozzle 33 is provided in the treatment room 50 for particle therapy, and irradiates a particle beam to a diseased part. The irradiation nozzle 33 may be an irradiation nozzle described in Japanese Patent No. 6387476. Further, the magnet unit 32 may include a beam slit unit (not illustrated) that adjusts a shape and/or a dose of the particle beam, or a steering magnet unit for finely adjusting a beam position of the particle beam. Note that the contents described in Japanese Patent No. 6364141 and Japanese Patent No. 6387476 are incorporated in the present application by reference.

The irradiation nozzle 33 includes a scanning magnet 331, a beam monitor 332, and energy modulation means 333.

The scanning magnet 331 is an electromagnet for finely adjusting a traveling direction of the particle beam that is emitted from the irradiation nozzle 33 by adjusting an amount of a current that flows and a direction of the current, and enabling scan (scanning) within a predetermined range.

Figure 6:
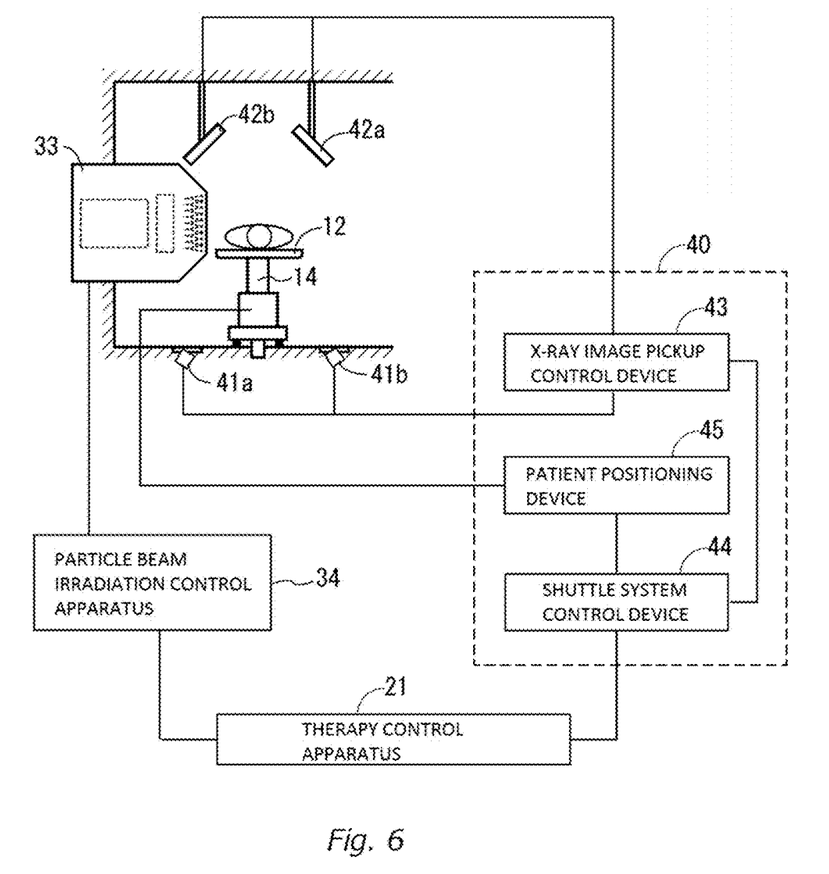
FIG. 6 is a control block diagram of the irradiation system for particle therapy.

The beam monitor 332 is a monitor that monitors a particle beam, and measures a dose, a position and flatness of the beam. The measured information is fed back to a particle beam irradiation control apparatus 34 from the beam monitor 332, and is used in control of the scanning magnet 331 and highly precise irradiation of the particle beam. The energy modulation means 333 adjusts a depth in the patient at which the particle beam reaches by adjusting energy of the particle beam, and is, for example, a range modulator, a scatterer, a ridge filter, a patient collimator, a patient bolus, an applicator, or the like.

Figure 5A:
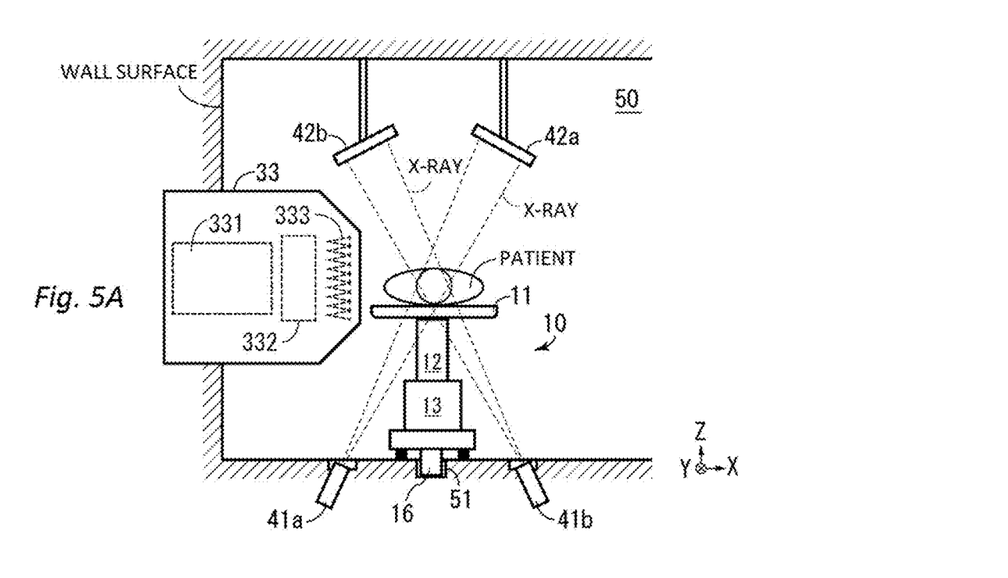
FIGS. 5A and 5B are schematic views of the irradiation system for particle therapy.
Figure 5B:
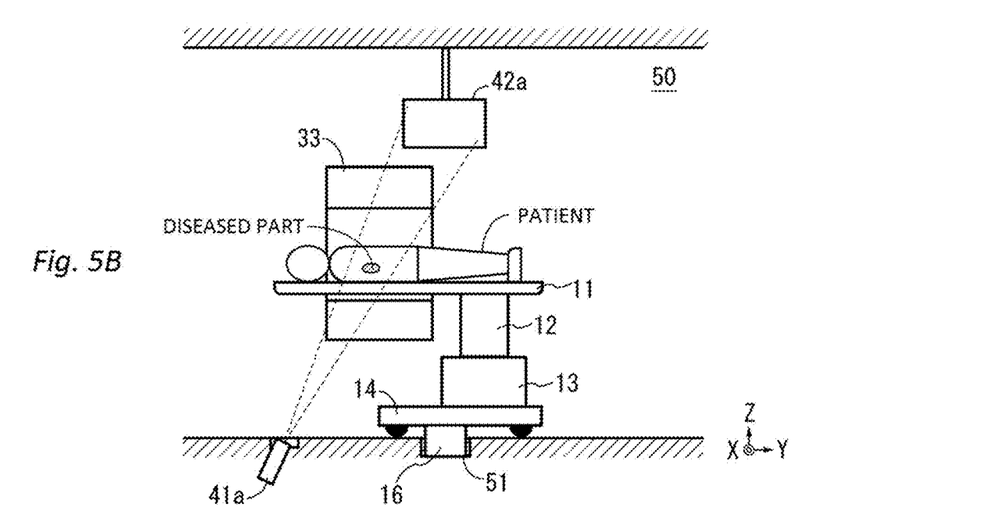

FIG. 5A is a view of the patient shuttle system 10 seen from a head side (front) of a patient, and FIG. 5B is a view seen from a side.

The patient positioning system 40 includes a plurality of X-ray generating apparatuses 41a and 41b (collectively referred to as the X-ray generating apparatus 41) that generate X-rays and irradiate the patient with the X-rays, and X-ray detectors 42a and 42b (collectively referred to as the X-ray detector 42) that respectively detect the X-rays irradiated from the X-ray generating apparatuses 41a and 41b. The X-ray generating apparatus 41 is an X-ray tube, an X-ray generating apparatus for cone beam CT or the like, and the X-ray detector 42 may be a CCD area image sensor, a CMOS area image sensor, or a flat panel sensor that detects the X-rays outputted from the X-ray generating apparatus 41. Note that patient positioning of the particle beam and the diseased part which should be irradiated with the particle beam may be performed by using an MRI apparatus using magnetic resonance, instead of the X-ray generating apparatus 41 and the X-ray detector 42 using X-rays.

Note that in FIGS. 5A and 5B, two pairs that are the X-ray generating apparatuses 41a and 41b, and the X-ray detectors 42a and 42b corresponding to the X-ray generating apparatuses 41a and 41b are drawn, but a number of pairs of the X-ray generating apparatus 41 and the X-ray detector 42 may be one, or three pairs of more. As the number of pairs of the X-ray generating apparatus 41 and the X-ray detector 42 is larger, precision is enhanced more, but processing is more complicated, so that the number of pairs of the X-ray generating apparatus 41 and the X-ray detector 42 is preferably two to three.

FIG. 6 is a control block diagram of the patient positioning system 40 and the irradiation system 20 for particle therapy.

The patient positioning system 40 includes an X-ray image pickup control device 43, a patient positioning device 44, and a shuttle system control device 45. The X-ray image pickup control device 43, the patient positioning device 44, and the shuttle system control device 45 are functional units that include various communication interfaces, programs and processors (ASIC or the like) for various kinds of control, and storage units that store the programs and various kinds of information, and are realized by the programs stored in the storage units and the processors cooperating with one another. The X-ray image pickup control device 43, the patient positioning device 44, and the shuttle system control device 45 may be provided in the treatment room 50 for particle therapy, or may be provided in a spot away from the treatment room 50 for particle therapy, and control the X-ray generating apparatus 41 and the X-ray detector 42 in the treatment room for particle therapy and the patient shuttle system 10 remotely.

The X-ray image pickup control device 43 controls the X-ray generating apparatus 41 and the X-ray detector 42, generates an X-ray image of the patient, and outputs the X-ray image to the patient positioning device 44, in accordance with a command of the patient positioning device 44 or at a predetermined period.

The patient positioning device 44 compares the X-ray image received from the X-ray image pickup control device 43 with a reference X-ray image relating to a site that should be irradiated with the particle beam, of the patient that is stored in advance, and calculates an error amount (positional error) between both of the X-ray image and the reference X-ray image. Subsequently, the patient positioning device 44 outputs information relating to the positional error between the X-ray image and the reference X-ray image to the shuttle system control device 45.

Here, as for the reference X-ray image, an X-ray image of the site (diseased part) which should be irradiated with the particle beam, of the patient, is obtained in the preparation room (or the treatment room 50 for particle therapy) where the X-ray image can be obtained, and is stored in the patient positioning system 40, before the particle therapy is performed. Note that when the particle therapy to a same diseased part is performed plurality of times, it is not necessary to obtain the reference X-ray image at each particle therapy if the reference X-ray image relating to the diseased part is obtained at first, but the reference X-ray image may be obtained in the preparation room or the like before entry into the treatment room 50 for particle therapy at each particle therapy.

The shuttle system control device 45 calculates the parallel movement amounts (x, y, z) and/or the rotation amounts (θx, θy, θz) of the patient table 11 of the patient shuttle system 10 so that the positional error is reduced (or becomes zero) based on the positional error between the X-ray image and the reference X-ray image, and transmits the information to the drive control device 13 of the patient shuttle system 10. Further, the shuttle system control device 45 receives the information on the parallel movement amounts (x, y, z) and/or the rotation amounts (θx, θy, θz) of actual movement from the patient shuttle system 10, and outputs the information to the patient positioning device 44.

The patient positioning device 44 transmits the information relating to the patient positioning to a therapy control apparatus 21 that supervises the entire irradiation system 20 for particle therapy. The information relating to the patient positioning includes information on the parallel movement amounts (x, y, z) and/or the rotation amounts (θx, θy, θz) that are received by the patient positioning device 44 from the shuttle system control device 45. Further, when a fault or the like arises in the patient shuttle system 10, an error signal is transmitted to the patient positioning device 44 through the shuttle system control device 45 from the drive control device 13 of the patient shuttle system 10, and is transmitted to the therapy control apparatus 21 from the patient positioning device 44. The therapy control apparatus 21 that receives the error signal considers safety of the patient, and stops irradiation of the particle beam through the particle beam irradiation control apparatus 34.

The therapy control apparatus 21 issues a command to the particle beam irradiation control apparatus 34 based on the information on the patient positioning, and in response to the command, the particle beam irradiation control apparatus 34 controls the apparatus 30 for particle therapy and adjusts the dose, the shape, the irradiation position and the like of the particle beam.

In the irradiation system 20 for particle therapy, the position irradiated with the particle beam can be adjusted from both an approach that adjusts the patient position by controlling the patient table 11 of the patient shuttle system 10, and an approach that adjusts the irradiation position, the shape, energy and the like of the particle beam by controlling the irradiation apparatus 30 for particle therapy (the irradiation nozzle 33 or the like). Accordingly, the precision of the irradiation position of the particle beam is enhanced, and the time spent in adjustment is also reduced.

The patient positioning is performed before the particle therapy, but may be performed at a predetermined period during the particle therapy. Thereby, even when movement that is not intended by the patient under particle therapy or physiological body movement (breathing or the like) occurs, the irradiation position of the particle beam can be quickly adjusted.

Figure 7:
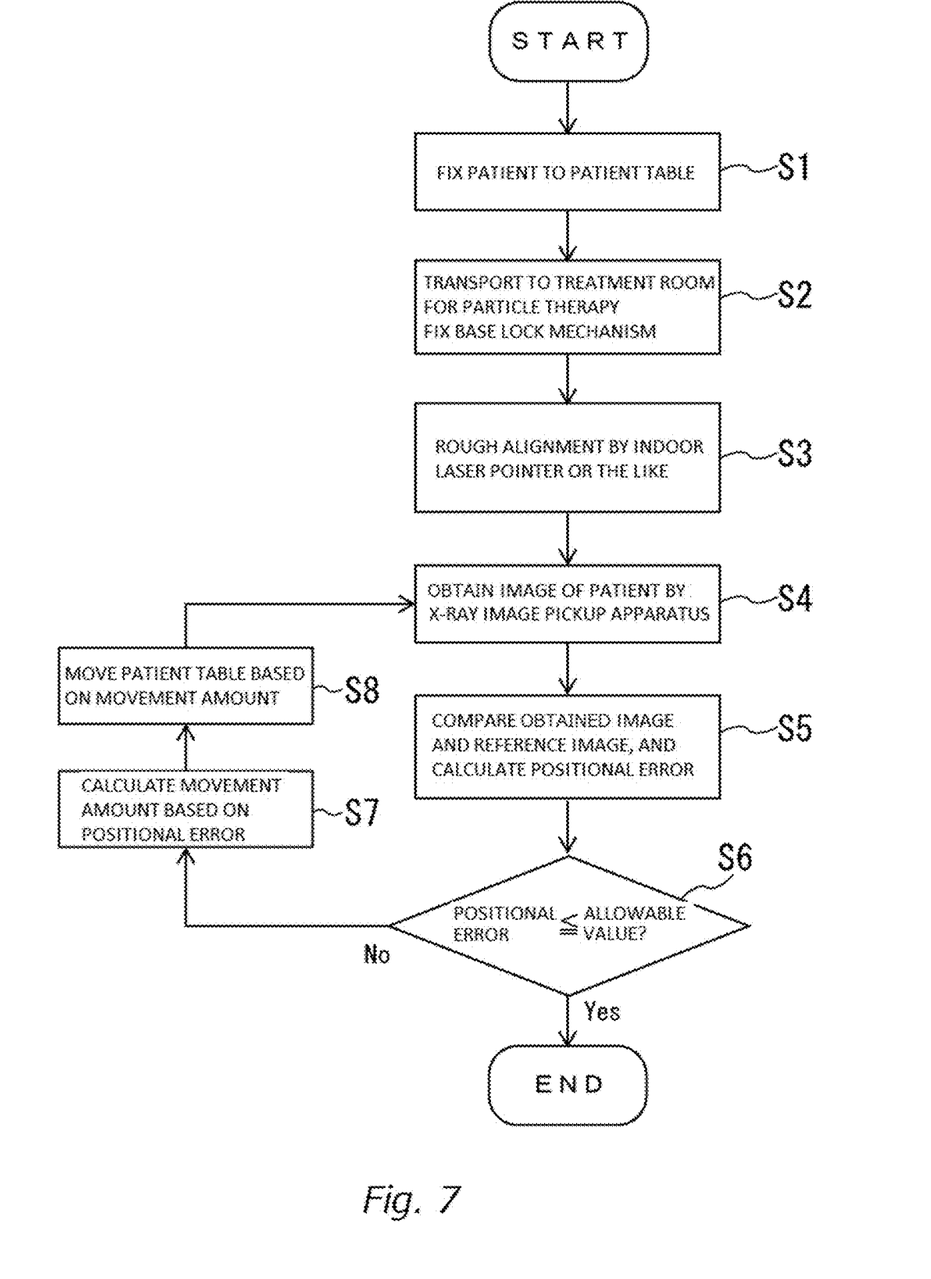
FIG. 7 is a flowchart of patient positioning.

FIG. 7 is a consecutive flowchart of patient positioning.

First, the patient who receives the particle therapy is placed on the patient table 11 of the patient shuttle system 10, and fixes the patient with the immobilization devices so that the patient does not move, in the preparation room or the like separate from the treatment room for particle therapy (step S1).

The patient shuttle system 10 on which the patient is placed is transported to the treatment room 50 for particle therapy, and the base lock mechanism 16 of the patient shuttle system 10 is fixed to the lock receiving member 51 of the treatment room 50 for particle therapy (step S2).

By using a laser pointer apparatus (not illustrated) provided in the treatment room 50 for particle therapy, rough alignment of the position that should be irradiated with the particle beam is performed from outside of the patient (on skin) (step S3). The rough alignment may be performed by a medical worker such as a doctor, or a technical expert, or may be automatically performed by the laser pointer apparatus, the therapy control apparatus 21, and the patient positioning system 40 cooperating with one another. Further, step S3 may be performed in another preparation room or the like instead of being performed in the treatment room 50 for particle therapy (in other words, step S3 is performed before step S2).

After the rough alignment, the X-ray image pickup control device 43 of the patient positioning system 40 controls the X-ray generating apparatus 41 and the X-ray detector 42, and picks up the X-ray image of the site that should be irradiated with the particle beam, of the patient (step S4). The patient positioning device 44 compares the X-ray image obtained in step S4 with the reference X-ray image which is stored in advance, and calculates the positional error between both of the X-ray image and the reference X-ray image (step S5). In calculation of the positional error, a known image processing algorithm such as a phase correlation method can be used, for example.

The patient positioning device 44 determines whether or not the positional error calculated in step S5 is a predetermined allowable value or less (step S6). When the positional error is the allowable value or less (Yes in step S6), the patient positioning device 44 transmits information indicating that the patient positioning is completed to the therapy control apparatus 21, and particle therapy (irradiation of the particle beam) is started.

When the positional error is larger than the allowable value (No in step S6), the patient positioning device 44 transmits the information on the positional error to the shuttle system control device 45, and the shuttle system control device 45 calculates the parallel movement amounts (x, y, z) and/or the rotation amounts (θx, θy, θz) of the patient table 11 of the patient shuttle system 10, and transmits information on the parallel movement amounts (x, y, z) and/or the rotation amounts (θx, θy, θz) to the drive control device 13 of the patient shuttle system 10 (step S7).

The drive control device 13 of the patient shuttle system 10 controls the drive device 12, and causes the patient table 11 to move parallel and/or rotate by amounts of the parallel movement amounts (x, y, z) and/or the rotation amounts (θx, θy, θz) which are received (step S8). Subsequently, steps S4 to S8 are repeated until the positional error becomes the allowable value or the less.

Figure 8A:
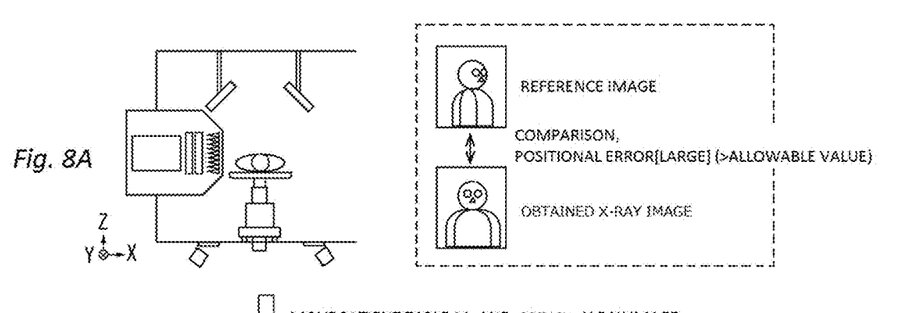
FIGS. 8A, 8B and 8C are diagrams explaining the patient positioning.
Figure 8B:
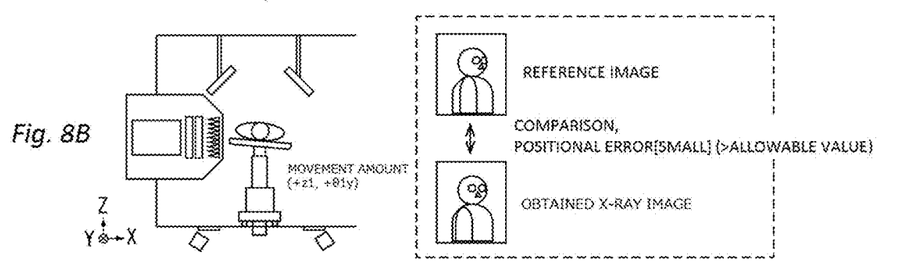
Figure 8C:
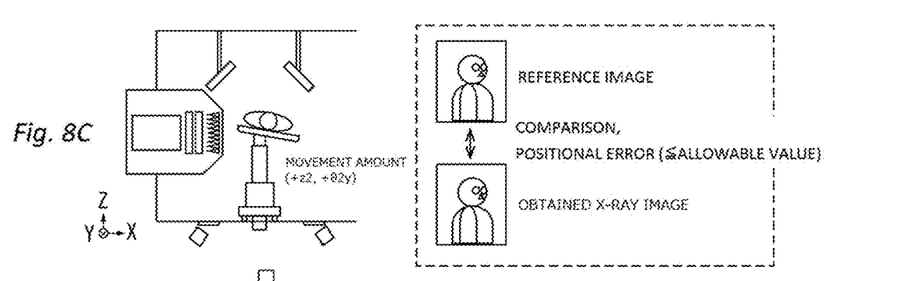

An outline of the patient positioning will be described again by using FIGS. 8A, 8B and 8C.

After the rough alignment, the X-ray image pickup control device 43 picks up the X-ray image of the patient, and outputs the X-ray image to the patient positioning device 44. The patient positioning device 44 compares the reference X-ray image which is stored in advance and the obtained X-ray image, calculates the positional error between both the reference X-ray image and the obtained X-ray image, and compares the positional error with the allowable value. FIG. 8A shows a case where the positional error is relatively large. Because the positional error is larger than the allowable value, the shuttle system control device 45 calculates the parallel movement amounts and/or the rotation amounts of the patient table 11 of the patient shuttle system 10 so as to reduce the positional error (or make the positional error zero), and transmits information on the parallel movement amounts and/or the rotation amounts to the drive control device 13 of the patient shuttle system 10. The drive control device 13 causes the patient table 11 to move parallel and/or rotate in accordance with the parallel movement amounts and/or the rotation amounts which are received. An X-ray image is picked up after the patient table 11 moves, similar processes are repeated, and the positional error is reduced gradually (FIGS. 8A to 8C). In FIG. 8B, the patient table 11 is caused to rotate (+θ1y) around the Y-axis, while the patient table 11 is caused to move parallel (+z1) along the Z-axis. In FIG. 8C, the patient table 11 is caused to rotate (+θ2y) around the Y-axis, while the patient table 11 is caused to move parallel (+z2) along the Z-axis. When the positional error is reduced to the allowable value or less finally, the patient positioning is completed.

As described above, in the irradiation system 20 for particle therapy using the patient shuttle system 10 according to the present embodiment, it is not necessary to provide a treatment table which is always incorporated in the treatment room for particle therapy as in the prior art, and therefore, the space of the treatment room for particle therapy can be reduced. As a result, even in an existing hospital facility which has an X-ray diagnosis apparatus, but does not have a sufficient space for installing an irradiation system for particle therapy, a particle therapy system is easily introduced. Further, in the irradiation system 20 for particle therapy using the patient shuttle system 10, a patient enters the treatment room for particle therapy while being on the patient shuttle system 10 from the preparation room or a hospital room, and can receive particle therapy, and therefore a psychological burden of the patient, which is associated with changing to a treatment table or transferring the patient table as in the conventional art can be reduced. Further, the deviation of the patient position associated with transfer of the patient table as in the prior art can also be reduced. Further, even when a fault or the like arises in the patient shuttle system 10 during particle therapy, the error information is transmitted to the therapy control apparatus 21, and irradiation of the particle beam is configured to be able to be stopped safely. Further, even during the particle therapy, the patient positioning can be performed periodically, and even when movement that is not intended by the patient or physiological body movement occurs, the deviation of the position irradiated with the particle beam is compensated by moving the patient table 11 in accordance with the movement, so that the correct site which should be irradiated can be irradiated with the particle beam.

The dimensions, materials, shapes, the relative positions of the components and the like that are described in the above described embodiment are arbitrary, and are changed in accordance with the structure of the apparatus to which the present invention is applied and various conditions. Further, the present invention is not limited to the above described embodiment which is specifically described.

In the embodiment which is described, specific terms are used for clarification. However, the present invention does not intend to be limited to the specific terms and examples which are selected. The person skilled in the art of the related field would recognize that other equivalent components can be used, and other methods can be developed without departing from the wide idea of the present invention.

The foregoing explanation is directed to the preferred embodiment of the present invention, but it should be noted that other modifications and changes are apparent to a person skilled in the art, and can be carried out without departing from the gist or scope of the present invention. Further, the features described in connection with one embodiment of the present invention can be used with other embodiments, even if not explicitly mentioned above.

REFERENCE SIGNS LIST

10 Patient shuttle system
11 Patient table
12 Drive device
13 Drive control device
131 Signal transmission/reception unit
132 Parallel movement control unit
133 Rotation control unit
134 Movement and rotation amounts calculation unit
14 Base
15 Patient table lock mechanism
16 Base lock mechanism
20 Particle beam irradiation system
21 Therapy control apparatus
30 Irradiation apparatus for particle therapy
31 Accelerator
32 Magnet unit
33 Irradiation nozzle
34 Particle beam irradiation control apparatus
40 Patient positioning system
41 X-ray generating apparatus
42 X-ray detector
43 X-ray image pickup control device
44 Patient positioning device
45 Shuttle system control device
50 Treatment room for particle therapy
51 Lock receiving member

What is claimed is:

1. A patient shuttle system, comprising:
a patient table on which a patient is placed;
a drive device configured to cause the patient table to move parallel and/or rotate;
a drive control device configured to control parallel movement and/or rotation of the patient table by the drive device, in accordance with a parallel movement amount and/or a rotation amount of the patient table that are received from a patient positioning system provided in a treatment room for particle therapy, the patient positioning system comprising an X-ray generator and an X-ray detector; and
a base lock mechanism configured to engage with a lock receiving member provided in the treatment room for particle therapy and fix the patient shuttle system to the treatment room for particle therapy.

2. The patient shuttle system according to claim 1, wherein the drive device is configured to cause the patient table to move parallel along at least one direction of a short side direction (an X-axis) of the patient table, a long side direction (a Y-axis) of the patient table, and a perpendicular direction (a Z-axis) to the long side direction and the short side direction, and/or cause the patient table to rotate around at least one direction of the short side direction (the X-axis), the long side direction (the Y-axis), and the perpendicular direction (the Z-axis).

3. The patient shuttle system according to claim 1, wherein the drive device is configured to cause the patient table to move parallel along a short side direction (an X-axis) of the patient table, a long side direction (a Y-axis) of the patient table, and a perpendicular direction (a Z-axis) to the long side direction and the short side direction, and cause the patient table to rotate around the short side direction (the X-axis), the long side direction (the Y-axis), and the perpendicular direction (the Z-axis).

4. The patient shuttle system according to claim 1, wherein a particle beam is a proton beam, a neutron beam, or a heavy-ion beam.

5. An irradiation system for particle therapy, comprising:
an irradiation apparatus for particle therapy;
a patient positioning system provided in a treatment room for particle therapy, the patient positioning system comprising an X-ray generator and an X-ray detector; and
the patient shuttle system according to claim 1.

6. The irradiation system for particle therapy according to claim 5,
wherein the patient positioning system further comprises
an X-ray image pickup control device configured to control the X-ray generating apparatus and the X-ray detector and generate an X-ray image of the patient, the X-ray generating apparatus being configured to irradiate a patient placed on the patient table with an X-ray, and the X-ray detector being configured to detect the X-ray,
a patient positioning device configured to compare the X-ray image with a reference X-ray image relating to a site that should be irradiated with a particle beam, of the patient, and calculate a positional error between the X-ray image and the reference X-ray image, and
a shuttle system control device configured to calculate a parallel movement amount and/or a rotation amount of the patient table so as to reduce the positional error, when the positional error is not a predetermined allowable value or less, and transmit the parallel movement amount and/or the rotation amount to the patient shuttle system.

7. An operation method of the irradiation system for particle therapy according to claim 6, comprising the steps of:
controlling the X-ray generating apparatus and the X-ray detector, and generating an X-ray image of the patient by the X-ray image pickup control device;

comparing the X-ray image with the reference X-ray image and calculating a positional error between the X-ray image and the reference X-ray image by the patient positioning device;

calculating a parallel movement amount and/or a rotation amount of the patient table so as to reduce the positional error, when the positional error is not a predetermined allowable value or less, and transmitting the parallel movement amount and/or the rotation amount to the patient shuttle system by the shuttle system control device; and controlling parallel movement and/or rotation of the patient table by the drive device by the drive control device, in accordance with the parallel movement amount and/or the rotation amount.

8. The method according to claim 7, further comprising the steps of:

receiving by the shuttle system control device an error signal from the patient shuttle system;

transmitting by the patient positioning device the error signal to a therapy control apparatus configured to supervise the irradiation system for particle therapy; and stopping by the therapy control apparatus irradiation of the particle beam through a particle beam irradiation control apparatus configured to control the irradiation apparatus for particle therapy.

9. The patient shuttle system for transporting a patient to the treatment room for particle therapy and/or for transporting a patient from the treatment room for particle therapy, according to claim 1, wherein the patient positioning system further comprises:

an X-ray image pickup control device configured to control the X-ray generating apparatus and the X-ray detector and generate an X-ray image of the patient, the X-ray generating apparatus being configured to irradiate a patient placed on the patient table with an X-ray, and the X-ray detector being configured to detect the X-ray, a patient positioning device configured to compare the X-ray image with a reference X-ray image relating to a site that should be irradiated with a particle beam, of the patient, and calculate a positional error between the X-ray image and the reference X-ray image, and a shuttle system control device configured to calculate a parallel movement amount and/or a rotation amount of the patient table so as to reduce the positional error, when the positional error is not a predetermined allowable value or less, and transmit the parallel movement amount and/or the rotation amount to the patient shuttle system.

* * * * *